(12) United States Patent
Chapuis

(10) Patent No.: US 9,701,926 B2
(45) Date of Patent: Jul. 11, 2017

(54) COMPOUND WITH A WOODY ODOUR

(71) Applicant: Firmenich SA, Geneva (CH)

(72) Inventor: Christian Chapuis, Geneva (CH)

(73) Assignee: Firmenich SA, Geneva (CH)

( * ) Notice: Subject to any disclaimer, the term of this patent is extended or adjusted under 35 U.S.C. 154(b) by 10 days.

(21) Appl. No.: 15/036,056

(22) PCT Filed: Oct. 22, 2014

(86) PCT No.: PCT/EP2014/072671
§ 371 (c)(1),
(2) Date: May 11, 2016

(87) PCT Pub. No.: WO2051/067470
PCT Pub. Date: May 14, 2015

(65) Prior Publication Data
US 2016/0289595 A1 Oct. 6, 2016

(30) Foreign Application Priority Data
Nov. 11, 2013 (EP) ..................................... 13192281

(51) Int. Cl.
| | |
|---|---|
| C11B 9/00 | (2006.01) |
| C07C 33/14 | (2006.01) |
| C07C 69/07 | (2006.01) |
| C07C 33/12 | (2006.01) |
| C07C 47/277 | (2006.01) |

(52) U.S. Cl.
CPC ............ *C11B 9/0046* (2013.01); *C07C 33/12* (2013.01); *C07C 33/14* (2013.01); *C07C 47/277* (2013.01); *C07C 69/07* (2013.01); *C07C 2102/42* (2013.01)

(58) Field of Classification Search
CPC .................................. C07C 33/12; C11B 9/00
See application file for complete search history.

(56) References Cited

U.S. PATENT DOCUMENTS 4,224,253 A * 9/1980 Baumann .................. C07C 1/34
512/14

FOREIGN PATENT DOCUMENTS

| EP | 10213 | 4/1980 |
| WO | WO2008092981 A1 | 8/2008 |
| WO | WO2012110375 A1 | 8/2012 |

OTHER PUBLICATIONS

International Search Report and Written Opinion, application PCT/EP2014/072671 mailed Jan. 23, 2015.
Chapuis et al., Helv. Chim. Acta, 2001, 84, 230-242.

\* cited by examiner

*Primary Examiner* — Lanee Reuther
(74) *Attorney, Agent, or Firm* — Winston & Strawn LLP

(57) ABSTRACT

The present invention concerns 2-methyl-5-[2-methyl-3-methylene-bicyclo[2.2.1]hept-5-en-2-yl)]-2-penten-1-ol in any of its stereometric forms or a lower ester thereof and their use as perfuming ingredient, in particular to impart sandalwood and cedar wood notes.

21 Claims, No Drawings

COMPOUND WITH A WOODY ODOUR

This application is a 371 filing of International Patent Application PCT/EP2014/072671 filed 22 Oct. 2014, which claims the benefit of European patent application no. 13192281.7 filed 11 Nov. 2013 both of which are incorporated by reference herein.

TECHNICAL FIELD

The present invention relates to the field of perfumery. More particularly, it concerns 2-methyl-5-[2-methyl-3-methylenebicyclo[2.2.1]hept-5-en-2-yl)]-2-penten-1-ol or a lower ester thereof and their use as perfuming ingredient, in particular to impart sandalwood and cedar wood notes. The present invention comprises also the invention's compound as part of a perfuming composition or of a perfuming consumer product.

PRIOR ART

To the best of our knowledge, none of the invention's compounds is known in the prior art.

Sandalwood essential oil is a very important material for perfumery. Many botanical species of sandalwood exist but only the Indian one is reputed to provide outstanding oil, while the other ones are reputed to lack the "natural" and/or "lait de santal". Since the Indian botanical species is now a protected species and is no more available on industrial scale, there is a real need for ingredients able to impart sandalwood notes as natural as possible and/or capable of improving the olfactive profile of the available natural oils. To the best of our knowledge, none of the presently known sandalwood perfumery ingredients is able of such performance.

DESCRIPTION OF THE INVENTION

We have now surprisingly discovered that a compound of formula

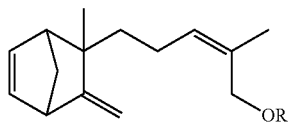

(I)

in the form of any one of its stereoisomers or a mixture thereof; and wherein R represents a hydrogen atom or a $C_{1-3}$ carboxylic group;
can be used as perfuming ingredient, for instance to impart odor notes sandal and cedar wood type.

According to a particular embodiment of the invention, said R group represents a hydrogen atom or group of formula HCO (formyl), $CH_3CO$ (acetyl). According to a particular embodiment of the invention, said R group represents a hydrogen atom.

According to any embodiment of the invention, and independently of the specific aspects, the compound (I) can be in the form of any one of its stereoisomers or mixture thereof. For the sake of clarity by the term stereoisomer it is intended any diastereomer, enantiomer, racemate or carbon-carbon double bond isomer of configuration E or Z.

According to any embodiment of the invention, compound (I) is in the form of a mixture of stereoisomers comprising more than 50% (w/w) of the (1SR,2SR,4RS) stereoisomer, i.e. a compound having the relative exo configuration (the bridging methylene and the allylic alcohol chain) as shown in formula (I-A)

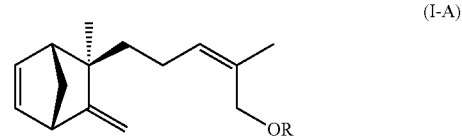

(I-A)

wherein the bold and hatched lines indicate a relative configuration. Preferably, said mixture of stereoisomers comprises more than 70% (w/w), or even more than 90% (w/w), of the (1SR,2SR,4RS) stereoisomer.

According to any embodiment of the invention, compound (I) is in the form of a mixture of stereoisomers comprising more than 50% (w/w) of the (1R,2R,4S) stereoisomer, i.e. a compound having the absolute configuration as shown in formula (I-B)

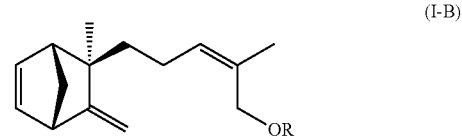

(I-B)

wherein the bold and hatched lines indicate an absolute configuration. Preferably, said mixture of stereoisomers comprises more than 70% (w/w), or even more than 90% (w/w), of the (1R,2R,4S) stereoisomer.

According to any one of the above embodiments of the invention, said compound can be in the form of its E or Z isomer or of a mixture thereof, e.g. the invention comprises compositions of matter consisting of one or more compounds of formula (I), having the same chemical structure but differing by the configuration of the double bond. In particular, compound (I) can be in the form of a mixture consisting of isomers E and Z and wherein said isomers Z represent at least 50% of the total mixture, or even at least 75% (i.e. a mixture Z/E comprised between 75/25 and 100/0).

As specific examples of the invention's compounds, one may cite, as non-limiting example, (−)-(2Z)-2-methyl-5-[(1R,2R,4S)-2-methyl-3-methylenebicyclo[2.2.1]hept-5-en-2-yl)]-2-penten-1-ol, also hereinafter named (−)-dehydro-β-santalol (in the form of a mixture of stereoisomers as described in Example 1) which possesses a powerful sandalwood odor combined with a cedar wood note.

Astonishingly the odor of the invention's compound has been found to be able to boost the natural, "lait de santal" and warm aspect of natural sandalwood extract, such as the Australian sandalwood oil. This boosting effect is very surprising since it is unknown from any synthetic derivative having a sandalwood note.

The odor of (−)-(2Z)-2-methyl-5-R1R,2R,4S)-2-methyl-3-methylene-bicyclo[2.2.1]hept-5-en-2-yl)]-2-penten-1-ol, when compared to the one of the prior art having a sandalwood commutation, presents its own particularities.

When the odor of the invention's compound is compared with that of the prior art compound (−)-(2Z)-β-santalol, then the invention's compounds distinguish themselves by a more intense sandalwood note and being also less sweet.

The present compounds distinguish also notably by having a cedar wood note which is absent from the natural compound (−)-(2Z)-β-santalol.

When the odor of the invention's compound is compared with that of the prior art sandalwood odorant 2-methyl-4-(2,2,3-trimethyl-3-cyclopenten-1-yl)-4-penten-1-ol (see EP 694520), then the invention's compounds distinguish themselves by a more intense natural, less chemical, sandalwood note. The present compounds distinguish also notably by having a cedar wood note which is absent from the prior art compound.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

By the way, a specific object of the present invention is a method to confer, enhance, boost, improve or modify the odor properties of a perfuming composition or of a perfumed article comprising a natural extract of sandalwood, in particular of the Autralian species, which method comprises adding to said composition or article an effective amount of at least a compound of formula (I).

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

According to any one of the above embodiments of the invention, the perfumery base comprises a natural extract of sandalwood oil, indeed as mentioned previously the invention's compound is capable of boosting the olfactive quality of the natural oil by pushing its "lait de santal" notes and warmness.

By "perfumery adjuvant" we mean here an ingredient capable of imparting additional added benefits such as a color, a particular light resistance, chemical stability, etc. A detailed description of the nature and type of adjuvants commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery.

Furthermore, the invention's compound can also be advantageously used in all the fields of modern perfumery, i.e. fine or functional perfumery, to positively impart or modify the odor of a consumer product into which said compound (I) is added. Consequently, another object of the present invention is represented by a perfuming consumer product comprising, as perfuming ingredient, at least one compound of formula (I), as defined above.

The invention's compound can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer product do not warrant a more detailed description here, which in any case would not be exhaustive, the skilled person being able to select them on the basis of his general knowledge and according to the nature and the desired effect of said product.

Non-limiting examples of suitable perfumery consumer product can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product product may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 5% by weight, or even more, of the compounds of the invention based on the weight of the composition into which they are incorporated. Concentrations lower than these, such as in the order of 0.1% to 2.5% by weight, can be used when these compounds are incorporated into perfumed articles, percentage being relative to the weight of the article.

The invention's compounds can be prepared according to a method as described in the Examples herein below.

EXAMPLES

The invention will now be described in further detail by way of the following examples, wherein the abbreviations have the usual meaning in the art, the temperatures are indicated in degrees centigrade (° C.); the NMR spectral data were recorded in CDCl$_3$ (if not stated otherwise) with a 360 or 400 MHz machine for $^1$H and $^{13}$C, the chemical shifts δ are indicated in ppm with respect to TMS as standard, the coupling constants J are expressed in Hz.

Example 1

Synthesis of Compounds of Formula (I)

The invention's compound was obtained according to the following reaction Scheme:

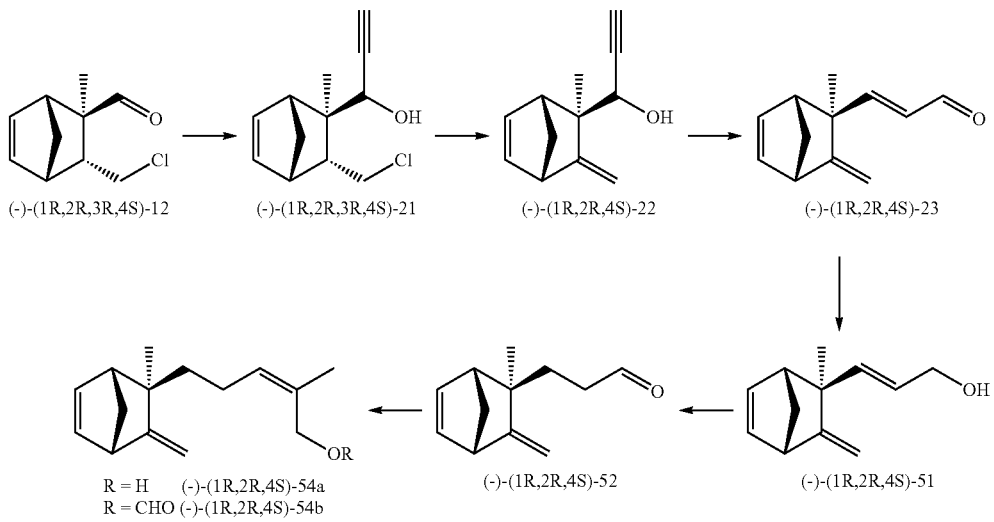

Preparation of (−)-(1R,2R,3R,4S)-21

Compound (−)-(1R,2R,3R,4S)-12 (obtained as described in WO2012/110375, pg 26) was converted into (−)-(1R,2R,3R,4S)-21 by the addition of ethynyl as described in WO2012/110375, pg 19 for the racemic compound (21a in WO2012/110375).

The optically active target compound was obtained in 82% yield, with NMR spectra identical to the one of the reported racemic compound and an $[\alpha]_D^{20}=-3.3$ at c=2.2% in CHCl$_3$.

Preparation of (−)-(1R,2R,4S)-22

Compound (−)-(1R,2R,3R,4S)-21 was converted into (−)-(1R,2R,4S)-22 by elimination as described in WO2012/110375, pg 20 for the racemic compound (22 in WO2012/110375). The optically active target compound was obtained in 84% yield, with NMR spectra identical to the one of the reported racemic compound and an $[\alpha]_D^{20}=-150.2$ at c=1.6% in CHCl$_3$.

Preparation of (−)-(1R,2R,4S)-23

Compound (−)-(1R,2R,4S)-22 was converted into (−)-(1R,2R,4S)-23 by the rearrangement as described in WO2012/110375, pg 23 for the racemic compound (23 in WO2012/110375).

The optically active target compound was obtained in 60% yield, with NMR spectra identical to the one of the reported racemic compound and an $[\alpha]_D^{20}=-417.5$ at c=3.8% in CHCl$_3$ (e.g. of about 90%).

Preparation of (−)-(E)-(1R,2R,4S)-2-Methyl-3-methylene bicyclo[2.2.1]hept-5-en-2-yl]prop-2-en-1-ol: (−)-(1R,2R,4S)-51

Aldehyde (−)-(1R,2R,4S)-23 (100 mg, 0.574 mmol) in THF (5 ml) was added dropwise to a suspension of LiAlH$_4$ (43.6 mg, 1.15 mmol) in THF (5 ml) at −10° C. After five minutes, 15% w/w aqueous NaOH (5 ml) was added dropwise at 0° C. and the reaction mixture which was then filtered, separated, dried (Na$_2$SO$_4$), concentrated and purified by CC/SiO$_2$ (cyclohexane/AcOEt 85:15) to afford quantitatively the pure desired allylic alcohol.

$[\alpha]_D^{20}=-435.5$ at c=2.5% in CHCl$_3$.
$^1$H-NMR: 1.07 (s, 3H); 1.33 (brs, 10H); 1.54 (dt, J=8.6, 1.4, 1H); 1.74 (dt, J=8.6, 1.4, 1H); 2.63 (brs, 1H); 3.19 (brs, 1H); 4.13 (dd, J=1.2, 5.7, 2H); 4.65 (s, 1H); 5.06 (s, 1H); 5.74 (dt, J=15.5, 5.7, 1H); 5.84 (dt, J=15.5, 1.2, 1H); 6.13-6.17 (m, 2H).
$^{13}$C-NMR: 157.5 (s); 140.8 (d); 136.0 (d); 135.9 (d); 126.7 (d); 104.5 (t); 64.0 (t); 52.4 (d); 52.0 (d); 48.8 (s); 48.1 (t); 26.8 (q).

Preparation of 3-((1R,2R,4S)-2-methyl-3-methylenebicyclo[2.2.1]hept-5-en-2-yl)propanal: (−)-(1R,2R,4S)-52

According to the general procedure described by C. Chapuis et al. in Helv. Chim. Acta 2001, 84, 230. MeOBiphep (13.88 mg, 0.024 mmol) was added to a solution of [Rh(cod)$_2$]BF$_4$ (9.68 mg, 0.024 mmol), in THF (2 ml), followed, after 1 hour at 20° C., by a solution of allylic alcohol (−)-(1R,2R,4S)-51 (60 mg, 0.34 mmol) in THF (8 ml). This mixture was refluxed under Ar for 18 hours, then filtered at 20° C., concentrated and purified by CC/SiO$_2$ (cyclohexane/AcOEt 97:3 to 95:5) to afford pure aldehyde (−)-(1R,2R,4S)-52 (34% yield, 68% yield based on recovered starting material).

$[\alpha]_D^{20}=-213.3$, at c=0.5% in CHCl$_3$.
$^1$H-NMR: 0.95 (s, 3H); 1.55 (dt, J=8.5, 1.6, 1H); 1.77 (dt, J=8.5, 1.6, 1H); 1.81-1.87 (m, 2H); 2.57-2.59 (m, 2H); 2.60 (brs, 1H); 3.18 (brs, 1H); 4.62 (s, 1H); 4.95 (s, 1H); 6.11-6.15 (m, 2H); 9.81 (t, J=1.6, 1H).
$^{13}$C-NMR: 202.6 (d); 160.0 (s); 136.7 (d); 135.6 (d); 103.2 (t); 52.3 (d); 50.4 (d); 47.8 (t); 45.0 (s); 40.4 (t); 33.3 (t); 25.3 (q).

Preparation of the Invention's Compounds (−)-(2Z)-2-methyl-5-[(1R,2R,4S)-2-methyl-3-methylenebicyclo[2.2.1]hept-5-en-2-yl)]-2-penten-1-ol Coll 64199 A3: (−)-(Z)-(1R,2R,4S)-54a or (−)-dehydro-β-santalol
(−)-(2Z)-2-methyl-5-[(1R,2R,4S)-2-methyl-3-methylidenebicyclo[2.2.1]hept-5-en-2-yl]-2-penten-1-yl formate: (−)-(Z)-(1R,2R,4S)-54b or (−)-dehydro-β-santalyl formiate nBuLi (1.6 M/hexane, 0.215 ml, 0.343 mmol) was added dropwise at 0° C. to a solution of ethyltriphenylphosphonium iodide (144 mg, 0.343 mmol) in THF (13.5 ml). The resultant solution was cooled to −78° C. and a solution of aldehyde (−)-(1R,2R,4S)-52 (55 mg, 0.312 mmol) in THF (1.5 ml) was added dropwise. After 15 minutes, a solution of nBuLi (1.6 M/hexane, 0.234 ml, 0.377 mmol) was added dropwise, then after 20 minutes, the temperature was equilibrated to 0° C. for 2 hours. Dry paraformaldehyde (56.2 mg, 1.872 mmol) was added and the reaction mixture was stirred at 20° C. for one day, before being put onto saturated aqueous NH$_4$Cl. The reaction mixture was extracted with CH$_2$Cl$_2$, dried (Na$_2$SO$_4$), concentrated and purified by CC/SiO$_2$ cyclohexane/AcOEt 99:1 to afford (−)-(Z)-(1R,2R,4S)-54a in 15% yield, and (−)-(Z)-(1R,2R,4S)-54b in 12% yield.

(−)-(Z)-(1R,2R,4S)-54a $[\alpha]_D^{20}=-229.0$, at c=0.6% in CHCl$_3$.
$^1$H-NMR: 0.96 (s, 3H); 1.25 (brs, 10H); 1.52 (ddd, J=1.7, 7, 10.4, 2H); 1.53 (d, J=8.9, 1H); 1.76 (d, J=8.9, 1H); 1.79 (d, J=1.1, 3H); 2.06-2.20 (m, 2H); 2.67 (brs, 1H); 3.15 (brs, 1H); 4.15 (s, 2H); 4.59 (s, 1H); 4.90 (s, 1H); 5.31 (t, J=7.4, 1H); 6.10 (dd, J=3.1, 5.4, 1H); 6.14 (dd, J=3.1, 5.4, 1H).
$^{13}$C-NMR: 160.9 (s); 137.0 (d); 135.4 (c); 134.1 (s); 128.9 (c); 102.5 (t); 61.6 (t); 52.2 (d); 50.0 (d); 47.8 (t); 45.6 (s); 42.1 (t); 25.3 (q); 23.4 (t); 21.2 (q).

(−)-(Z)-(1R,2R,4S)-54b $[\alpha]_D^{20}=-172.0$, at c=0.5% in CHCl$_3$.
$^1$H-NMR: 0.97 (s, 3H); 1.51-1.55 (m, 4H); 1.76 ((d, J=1.1, 3H); 2.10-2.22 (m, 2H); 2.67 (s, 1H); 3.16 (s, 1H); 4.59 (s, 1H); 4.70 (dd, J=11.7, 16.0, 2H); 4.91 (s, 1H); 5.43 (t, J=7.2, 1H); 6.10 (dd, J=3.0, 7.4, 1H); 6.14 (dd, J=3.0, 7.4, 1H); 8.11 (t, J=0.8, 1H).
$^{13}$C-NMR: 161.1 (c); 160.9 (s); 137.0 (d); 135.4 (d); 131.9 (d); 128.9 (s); 102.5 (t); 62.5 (t); 52.2 (c); 50.0 (d); 47.8 (t); 45.6 (s); 41.7 (t); 25.3 (q); 23.7 (t); 21.4 (q).

Example 2

Preparation of a Perfuming Composition

A perfume composition for woman was prepared by admixing the following ingredients:

| Parts by weight | Ingredient |
|---|---|
| 400 | Benzyl acetate |
| 50 | 2-Methyl-1-phenyl-2-propanol |

-continued

| Parts by weight | Ingredient |
|---|---|
| 200 | Citronellyl acetate |
| 100 | Styrallyl acetate |
| 150 | Cinnamic alcohol |
| 100 | 10%* Anisic aldehyde |
| 50 | 10%* C 10 aldehyde |
| 100 | 10%* C 12 aldehyde |
| 100 | 10%* Aldehyde MNA |
| 25 | Armoise oil |
| 250 | Bergamot essential oil |
| 100 | 10%* Raspberry ketone |
| 50 | Benzyl cinnamate |
| 250 | Coranol ™ 1) |
| 100 | Coumarine |
| 50 | 2-Heptyl-1-cyclopentanone |
| 100 | *Geranium* oil |
| 500 | Hydroxycitronellal |
| 750 | Iralia ® 2) |
| 200 | Isoeugenol |
| 200 | Jasmal ® 3) |
| 250 | Linalool |
| 900 | Lyral ® 4) |
| 150 | Methylisoeugenol |
| 500 | Muscenone ® 5) Delta |
| 1500 | Benzyl salicylate |
| 1000 | Australian Santal oil |
| 200 | *Styrax* essential oil |
| 25 | Vanilline |
| 1000 | Vertofix ® 6) Coeur |
| 400 | Wardia ® 7) |
| 250 | Ylang oil |
| 10000 | |

*in dipropyleneglycol
1) 4-cyclohexyl-2-methyl-2-butanol; origin: Firmenich SA, Geneva, Switzerland
2) mixture of methylionones isomers; origin: Firmenich SA, Geneva, Switzerland
3) tetrahydro-3-pentyl-2h-pyran-4-yl acetate; origin: International Flavors & Fragrances, USA
4) 4/3-(4-hydroxy-4-methylpentyl)-3-cyclohexene-1-carbaldehyde; origin: International Flavors & Fragrances, USA
5) 3-methyl-5-cyclopentadecen-1-one; origin: Firmenich SA, Geneva, Switzerland
6) methyl cedryl ketone; origin: International Flavors & Fragrances, USA
7) compounded perfumery base; origin: Firmenich SA, Geneva, Switzerland The addition of 200 parts by weight of (−)-dehydro-β-santalol to the above-described composition imparted to the latter a much more natural connotation which was very similar to the one obtained using a Indian sandalwood oil instead of the Australian one (the best ever type of sandalwood oil is the Indian one, but now not more available on the market since protected species). The invention's compound also adds an unusual cedar wood twist, not obtained when instead was added (−)-β-santalol.

Example 3

Preparation of a Perfuming Composition

A perfume composition for woman, of the agarwood type, was prepared by admixing the following ingredients:

| Parts by weight | Ingredient |
|---|---|
| 60 | Citronellyl acetate |
| 120 | Geranyl acetate |
| 30 | Phenylethyl acetate |
| 60 | 10%* C 7 aldehyde |
| 60 | Poplar oil |
| 60 | Benzylacetone |
| 300 | Castoreum oil |
| 150 | Cedar oil |
| 60 | Citral |
| 1500 | Citronellol |

-continued

| Parts by weight | Ingredient |
|---|---|
| 150 | Coranol ™ 1) |
| 120 | 10%* Damascenone |
| 60 | 10%* Ethyl decanoate |
| 90 | 10%* Etaspirene 2) |
| 900 | Geraniol |
| 15 | *Geranium* oil |
| 60 | Clove oil |
| 180 | Alpha Irone |
| 300 | Labdanum oil |
| 90 | Methylisoeugenol |
| 45 | Nutmeg oil |
| 330 | Nerol |
| 30 | Linalyl oxide |
| 30 | Rose oxide |
| 690 | Phenethylol |
| 30 | 10%* Cis-3-hexenol |
| 225 | 1%* Para Cresol |
| 15 | Safranal |
| 1500 | Sandela ® 3) |
| 1200 | Australian Santal oil |
| 30 | Origanol |
| 30 | Terpineol Alpha |
| 240 | Vetyver oil |
| 30 | Beta Ionone |
| 210 | (1S,2S,3S)-2,6,6-Trimethyl-bicyclo[3.1.1]heptane-3 spiro-2'-cyclohexen-4'-one |
| 9000 | |

*in dipropyleneglycol
1) 4-cyclohexyl-2-methyl-2-butanol; origin: Firmenich SA, Geneva, Switzerland
2) 6-ethyl-2,10,10-trimethyl-1-oxaspiro[4.5]deca-3,6-diene; origin: Firmenich SA, Geneva, Switzerland
3) 5-(2,2,3-trimethyl-3-cyclopentenyl)-3-methylpentan-2-ol; origin: Givaudan SA, Vernier, Switzerland The replacement of 200 parts by weight of Australian Santal oil with the same amount of (−)-dehydro-β-santalol in the above-described composition astonishingly boosted the santal notes and reinforced the "lait de santal" effect imparting also a more "natural" effect. Such effect was not obtainable when using the commercially available synthetic sandalwood odorants such as the camphoreric ones described in the literature.

What is claimed is:
1. A compound of formula

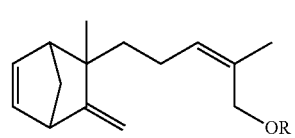

(I)

in the form of any one of its stereoisomers or a mixture thereof; wherein R represents a hydrogen atom, and wherein the compound of formula (I) imparts sandal and cedar wood odor notes.

2. A compound according to claim 1, wherein said compound is in the form of a mixture of stereoisomers comprising more than 50% (w/w) of the (1SR,2SR,4RS) stereoisomer and of a mixture of isomers E and Z wherein said isomers Z represent at least 75% (w/w) of the total mixture.

3. A perfuming ingredient comprising a compound of formula (I), as defined in claim 2.

4. A perfuming composition comprising
   i) at least one compound of formula (I), as defined in claim 2;
   ii) at least one ingredient selected from the group consisting of a perfumery carrier and a perfumery base; and
   iii) optionally at least one perfumery adjuvant.

5. A perfuming consumer product, wherein it comprises at least one compound of formula (I), as defined in claim 2.

6. A perfuming consumer product according to claim 2, wherein said product is a perfume, a fabric care product, a body-care product, an air care product or a home care product.

7. A perfuming consumer product according to claim 2, wherein said product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

8. A compound according to claim 1, wherein said compound is (−)-(2Z)-2-methyl-5-[(1R,2R,4S)-2-methyl-3-methylenebicyclo[2.2.1]hept-5-en-2-yl]-2-penten-1-ol.

9. A perfuming ingredient comprising a compound of formula (I), as defined in claim 8.

10. A perfuming composition comprising
   i) at least one compound of formula (I), as defined in claim 8;
   ii) at least one ingredient selected from the group consisting of a perfumery carrier and a perfumery base; and
   iii) optionally at least one perfumery adjuvant.

11. A perfuming consumer product, wherein it comprises at least one compound of formula (I), as defined in claim 8.

12. A perfuming consumer product according to claim 8, wherein said product is a perfume, a fabric care product, a body-care product, an air care product or a home care product.

13. A perfuming consumer product according to claim 8, wherein said product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

14. A perfuming ingredient comprising a compound of formula (I), as defined in claim 1.

15. A perfuming consumer product, wherein it comprises at least one compound of formula (I), as defined in claim 14.

16. A perfuming consumer product according to claim 14, wherein said product is a perfume, a fabric care product, a body-care product, an air care product or a home care product.

17. A perfuming consumer product according to claim 14, wherein said product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

18. A perfuming composition comprising
   i) at least one compound of formula (I), as defined in claim 1;
   ii) at least one ingredient selected from the group consisting of a perfumery carrier and a perfumery base; and
   iii) optionally at least one perfumery adjuvant.

19. A perfuming consumer product, wherein it comprises at least one compound of formula (I), as defined in claim 1.

20. A perfuming consumer product according to claim 19, wherein said product is a perfume, a fabric care product, a body-care product, an air care product or a home care product.

21. A perfuming consumer product according to claim 19, wherein said product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

* * * * *

UNITED STATES PATENT AND TRADEMARK OFFICE
CERTIFICATE OF CORRECTION

PATENT NO. : 9,701,926 B2
APPLICATION NO. : 15/036056
DATED : July 11, 2017
INVENTOR(S) : Chapuis It is certified that error appears in the above-identified patent and that said Letters Patent is hereby corrected as shown below:

On the Title Page
Item (87), PCT Pub. No., delete "WO2051/067470" and insert -- WO2015/067470 --.
Item (56), References Cited, OTHER PUBLICATIONS, after "Chapuis et al.", delete "Hely." and insert -- Helv. --.
Item (57), ABSTRACT, Line 3, delete "stereometric" and insert -- stereomeric --.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*